United States Patent [19]

Wampfler

[11] Patent Number: 5,030,841
[45] Date of Patent: Jul. 9, 1991

[54] PROCESS AND DEVICE FOR MEASURING THE TWIST OF A RUNNING, ELONGATE TEST BODY

[75] Inventor: Hans Wampfler, Zurich, Switzerland

[73] Assignee: Zellweger Uster AG, Ulster, Switzerland

[21] Appl. No.: 337,521

[22] PCT Filed: Jun. 29, 1988

[86] PCT No.: PCT/CH88/00116
§ 371 Date: Feb. 9, 1989
§ 102(e) Date: Feb. 9, 1989

[87] PCT Pub. No.: WO89/00215
PCT Pub. Date: Jan. 12, 1989

[30] Foreign Application Priority Data

Jul. 6, 1987 [CH] Switzerland ............. 02565/87

[51] Int. Cl.$^5$ ............................................. G01N 21/86
[52] U.S. Cl. ....................................... 250/571; 356/429
[58] Field of Search ............. 57/264, 265; 73/159, 73/160; 250/561, 571, 572; 356/429, 430

[56] References Cited

U.S. PATENT DOCUMENTS 3,557,377  1/1971  Raasch ........................... 250/571

FOREIGN PATENT DOCUMENTS 1560540   6/1970  Fed. Rep. of Germany .
3628654A1 3/1988  Fed. Rep. of Germany .
50-30184  9/1975  Japan .
5030184   9/1975  Japan .

Primary Examiner—David C. Nelms
Attorney, Agent, or Firm—Burns, Doane, Swecker & Mathis

[57] ABSTRACT

A test body is illuminated by at least one light source obliquely to its direction of travel, and the reflected light is imaged onto a diaphragm and fed to a photoelectric receiver. Its signal is investigated, in an evaluating unit, for periodicties which are caused by irregularities included in the test body as a result of the twist and the wavelength of which represents a measure of the twist. A rapid and precise measurement of the twist of yarns is made possible thereby.

15 Claims, 2 Drawing Sheets

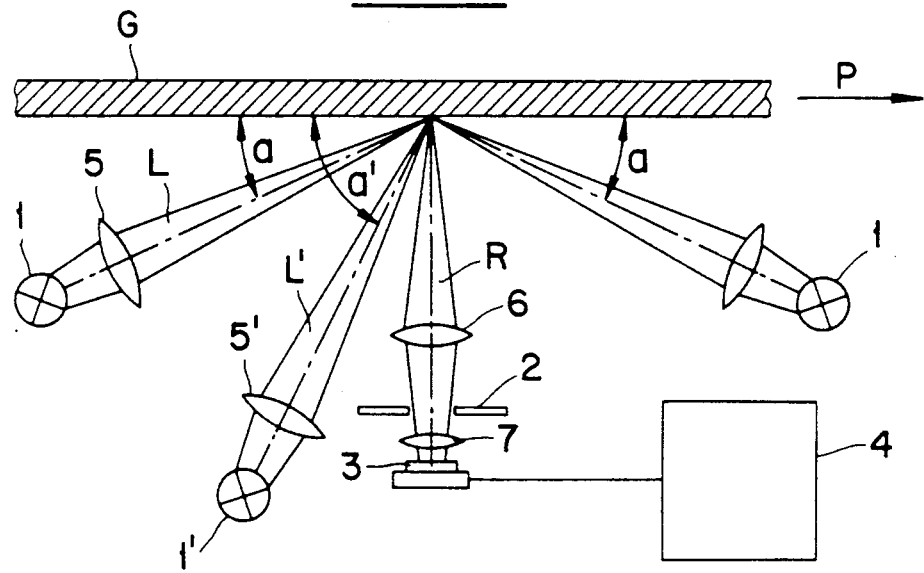

PROCESS AND DEVICE FOR MEASURING THE TWIST OF A RUNNING, ELONGATE TEST BODY

BACKGROUND OF THE INVENTION

The invention relates to a process for measuring the twist of a running, elongate test body, such as, for example, of a yarn or of a wire rope, by optical scanning of its surface and analysis of the scanning signal obtained in this case.

In a process of this type which is known from DE-A-3,628,654, a thread is grazingly acted upon by light, and specifically in such a manner that a part of the light beam is shaded off by thread and the part permitted to pass by the thread impinges on a light receiver. As a result of this, it is possible to detect certain structural alterations which are a measure of the thread period. Since this process, in which the profile is scanned to a certain extent, can be employed only when a detectable profile is present at all, this process is not suitable for the measurement of the twist of yarns.

A process of the initially mentioned type for the measurement of the twist of yarns is to be indicated by the invention.

SUMMARY OF THE INVENTION

According to the invention, this object is achieved in that the test body is illuminated by at least one light source and the light reflected by the test body is imaged onto a diaphragm and is measured by at least one photoelectric receiver, the output signal of which is investigated for periodicities caused by irregularities included in the test body, and in that the twist is derived from the wavelength or from the frequency of these periodicities.

Thus, the invention proceeds from the novel finding that the twist of yarns and the like leads to the bindingin of irregularities, which occur periodically on account of the twist. If the surface of a continuous test body is investigated for such periodicities, then the twist can be determined from these; this would not be possible by a simple scanning of the yarn profile.

The invention further relates to a device for carrying out the process according to the invention. This device is characterized by at least one light source for illuminating the test body, a diaphragm, an optical system for imaging the light reflected by the test body onto this diaphragm, at least one photoelectric receiver disposed in the beam path downstream of the diaphragm and an evaluation unit associated with this photoelectric receiver.

BRIEF DESCRIPTION OF THE DRAWINGS

The invention is explained in greater detail herein below with reference to an illustrative embodiment in the drawings; in the drawings:

FIG 1B shows yet another preferred embodiment of the present invention.

DETAILED DESCRIPTION OF THE PREFERRED EMBODIMENTS

Figure 1A:
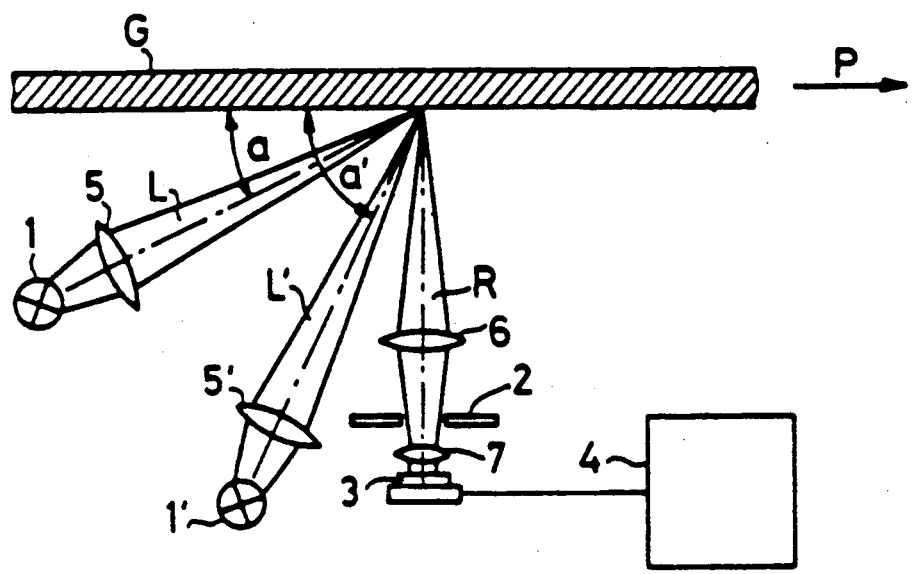
FIG. 1A shows a diagrammatic representation of a device according to the invention.

FIG. 1A shows a piece of a yarn G, which is conveyed by guide and transport means (not shown) in the direction of the arrow P through a device for measuring the yarn twist. As represented, this measuring device includes two light sources 1, 1' for illuminating the yarn G with a respective beam L, L', a diaphragm 2, onto which the beam R reflected by the yarn is imaged, a photoelectric receiver 3 disposed in the beam path downstream of the diaphragm and an evaluation unit 4 associated with this photoelectric receiver. Respective appropriate optical systems 5, 5' and 6 are provided in the beam path of the two beams L, L' and of the reflected beam R. A further lens 7 is situated between diaphragm 2 and photoelectric receiver 3. The light sources 1, ' are preferably formed by light-emitting diodes, so-called LEDs.

Figure 2:
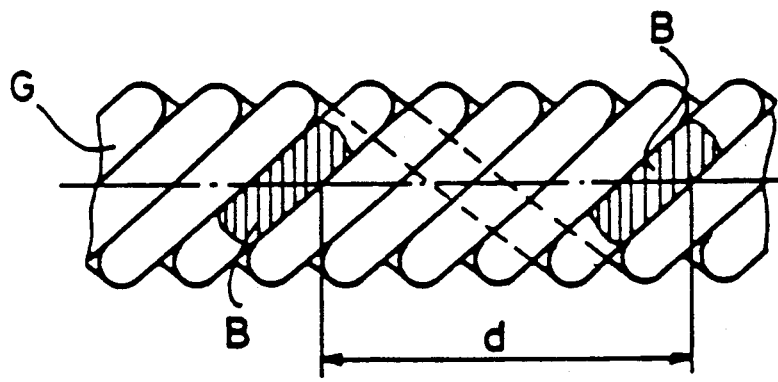
FIGS. 2,3 show diagrams for explaining the operation.
Figure 3:
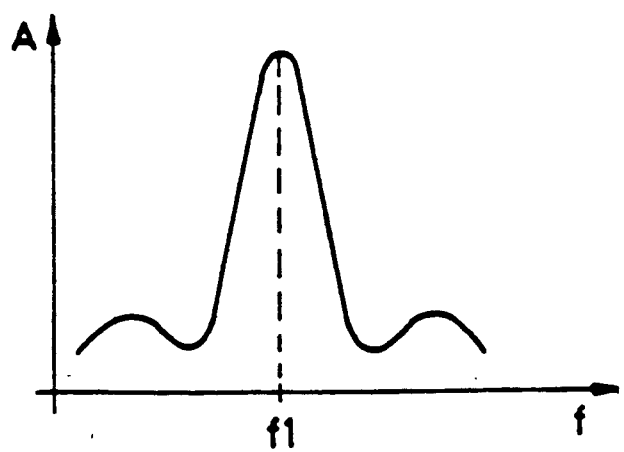

Before the measuring device is described in greater detail, the measurement process is to be explained now with reference to FIGS. 2 and 3: any yarn G exhibiting a twist or also any wire rope or any rope and the like exhibits, on account of the twist, certain irregularities with respect to its cross-section, and specifically, in particular, deviations from the cross-sectional shape. These characteristic deviations occur periodically, in which case the spacing between two successive such irregularities or, in other words, the length of the period thereof, represents a direct measure of the twist. This is so because the yarn twisted exactly once through 360° over such a period.

If the yarn G is illuminated at a small angle to its longitudinal axis, then the said irregularities become clearly visible as bright or dark positions, as is indicated in FIG. 2 by the hatched regions B. The length of the period, or, in other words, the wavelength of the irregularities, is designated by d. If T designates the twist of the yarn as the number of turns per unit length, then the following is applicable for the period d:d=1/T. Customary values for T are, for example, between 300 and 1,500 turns per meter. In the case of n-fold threads, the principal period occurs at d'=d/n, where here d designates the period of the thread twist; thus, for example in the case of 2-fold threads, the principal period is to be expected at d'=d/2.

The brightness of the impinging light beam R on the photoelectric receiver 3 (FIG. 1A) then increases periodically, and if the output signal of the photoelectric receiver 3 is evaluated in the evaluation unit 4 by Fourier transformation (FFT) or autocorrelation, a clearly detectable maximum is obtained at the period of the irregularities. In the case of very well defined structures, such as, for example, in the case of wire threads or filamentary threads, this analysis can, in certain circumstances, even take place by simple determination of a trigger threshold and subsequent counting.

The analysis by means of Fourier transformation is diagrammatically represented in FIG. 3; in this case, the frequency f is plotted on the abscissa and the amplitude A on the ordinate. A clearly detectable maximum is obtained at a specified frequency f1; in this case, the following then applies for the twist; T=f1/v, if v designates the draw-off speed of the yarn G. In the case of analysis by means of autocorrelation, the length d of the period is obtained directly.

In the case of yarns with twist, cross-sectional fluctuations also virtually always occur, which, however, do not necessarily lead to irregularities which are periodic, i.e. evaluable for the determination of the twist. Accordingly, it is advantageous to compensate the cross-sectional fluctuations; this takes place, as represented in FIG. 1A, by the use of two light sources 1 and 1', which illuminate the yarn G at differing angles of incidence. The angle of incidence a of the beam L is relatively small and is between 5° and 40°, preferably 5°, and the angle of incidence a' of the beam L' is steeper and is between 60° and 85°, preferably 85°.

If the two light sources L and L' are differently modulated, then, with corresponding demodulation of the signal, a single common photoelectric receiver 3 can be employed; in this case, the signal component originating from the light source 1 is divided, in this, by that originating from the light source 1'. However, it is also possible to use two light sources 1, 1', which emit light of differing wavelengths. In this case, the reflected beam R must be divided on the receiver side, and the individual components originating from the two light sources 1, 1' must be distributed by appropriate filters to two different photoelectric receivers.

A further illumination variant consists in using two light sources 1 with a small and a light source with a very steep angle of incidence of up to about 90°; in this case, in relation to FIG. 1B the two light sources 1 are disposed symmetrically on both sides of the reflected beam R and the third light source is situated between the other two. This arrangement leads, on the one hand, to an even better emphasising of periodic structures and, on the other hand, to the elimination of disturbing influences originating, for example, from neps and the like.

The following conditions are applicable to the diaphragm 2: if the yarn exhibits T twists per unit length, and is imaged onto the diaphragm 2 at the magnification K:1, then the diaphragm 2 must be narrower than K/T in the direction of the length of the yarn, in order that it should still be possible to achieve good detection of periodic components of the twist. In the case of yarns, in the transverse dimension the diaphragm 2 is advantageously restricted to the approximate detection of the yarn body, so that the hairiness does not have an excessively disturbing effect. In order to achieve further reduction of the disturbing influences of the hairiness, the yarn G can be singed. If the yarn G is very strongly singed, then it is possible to obtain insights into the twist in the yarn body; this can, on the one hand, be very much desired in the case of rotor yarns, but is, on the other hand, destructive and should therefore be restricted to random samples.

Finally, it should furthermore be mentioned that the test body G should be guided in a vibration-free manner as far as possible, since with light incident at a small angle vibrations have a disturbing effect. For this reason, it is advantageous to guide the test body G directly at the measurement position via a deflecting component.

The described measurement device can be constructed in a very compact manner, and is therefore outstandingly suitable for use as measurement module in a device for the automatic determination of characteristic quantities of textile test material, as is described, for example, in Swiss Patent Application No. 02,823/86-2, and is known under the designation USTER TESTER (USTER—registered trade mark of Zellweger Uster AG).

What is claimed is:

1. Process for measuring the twist of a running, elongate test material comprising the steps of:
   optically scanning a surface of the test material with at least one light source;
   imaging light from said at least one light source which has been reflected by the test material onto a diaphragm;
   measuring said reflected light downstream of said diaphragm using at least one photoelectric receiver said at least one photoelectric receiver producing an output signal related to said measured reflected light;
   analyzing the output signal for periodic components caused by irregularities present in the test material; and
   deriving twist of the test material using the wavelength or frequency of said periodic components.

2. Process according to claim 1, wherein said step of optically scanning includes a step of illuminating the test material via first and second light sources oriented at first and second angles of incidence relative to said test material, respectively.

3. Process according to claim 2, wherein said first and second light sources are differently modulated, said reflected light is measured by a single, common photoelectric receiver, and said step of measuring further includes a step of separating reflected light from said first light source and reflected light from said second light source.

4. Process according to claim 2, wherein said first and second light sources produce light of different wavelengths relative to one another, individual components of said reflected light associated with said first and second light sources being distributed to first and second photoelectric receivers, respectively, and said step of measuring further includes a step of separating reflected light received by said first photoelectric receiver and reflected light received by said second photoelectric receiver.

5. Process according to claim 1, wherein said step of optically scanning includes a step of illuminating the test material via first, second and third light sources, said first light source being oriented at a first angle of incidence relative to said test material, and said second and third light sources being disposed symmetrically relative to a beam of the reflected light and being oriented at a second angle of incidence relative to said test material, said second angle of incidence being substantially smaller than said first angle of incidence.

6. Process according to claim 1, wherein said step of analyzing includes a step of evaluating said output signal using a Fourier analysis.

7. Process according to claim 1, wherein said step of analyzing includes a step of evaluating said output signal using autocorrelation.

8. Process according to claim 1, wherein said elongate test material is yarn.

9. Process according to claim 1, wherein said elongate test material is a wire rope.

10. Apparatus for measuring the rotation of a running, elongate test material comprising:
    at least one light source for optically scanning a surface of a test material;
    an optical system for imaging light from said at least one light source which has been reflected by said test material onto a diaphragm;
    at least one photoelectric receiver disposed in a light beam path downstream of said diaphragm for producing an output signal related to said reflected light; and,
    means for analyzing said output signal to detect periodic components caused by irregularities present in the test material and for deriving a rotation of the test material from the wavelength or frequency of said periodic components.

11. Apparatus according to claim 10, wherein said at least one light source illuminates said test material at an oblique angle relative to direction of travel of the test material.

12. Apparatus according to claim 10, wherein said at least one light source includes first and second light sources oriented at first and second angles of incidence relative to said test material, said first angle being smaller than said second angle.

13. Apparatus according to claim 10, wherein said diaphragm has a dimension in a longitudinal direction of said test material which is less than a value K/T, where T corresponds to a number of rotations of the test material per unit length and the test material is imaged onto the diaphragm with a magnification factor K:1.

14. Apparatus according to claim 13, wherein said diaphragm has a dimension in a transverse direction of said test material such that light reflected by fibrous elements projecting from a surface of the test material is substantially prevented from reaching said at least one photoelectric receiver.

15. Apparatus according to claim 18, wherein a deflecting component is provided to guide the test material toward a measurement position.

* * * * *